United States Patent [19]

Woodward

[11] 3,950,362

[45] Apr. 13, 1976

[54] OXABICYCLOOCTANES AND PROCESS FOR THEIR MANUFACTURE

[75] Inventor: Robert Burns Woodward, Cambridge, Mass.

[73] Assignee: Ciba-Geigy Corporation, Ardsley, N.Y.

[22] Filed: Feb. 2, 1973

[21] Appl. No.: 329,250

[30] Foreign Application Priority Data
May 10, 1972 Switzerland.......................... 6936/72

[52] U.S. Cl........... 260/346.2 R; 260/333; 260/343; 260/514 D
[51] Int. Cl.² ..................................... C07D 307/77
[58] Field of Search ............................ 260/346.2 R

[56] References Cited
OTHER PUBLICATIONS
Coney et al., Tetrahedron Letters, No. 4, pp. 311–313, 1970.

Primary Examiner—John D. Randolph
Assistant Examiner—Bernard Dentz
Attorney, Agent, or Firm—Joseph G. Kolodny; John J. Maitner; Theodore O. Groeger

[57] ABSTRACT

Compounds of the formula

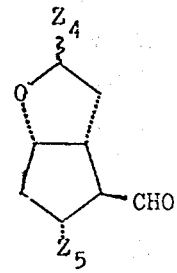

wherein $Z_4$ and $Z_5$ each independently represent free, etherified or esterified hydroxy groups, are produced by diazotisation of 2-exo-amino-3,4-endo-dihydroxy-8-$Z_4$-7-oxabicyclo [4,3,0]nonane followed by ring contraction, they are intermediates in the synthesis of prostaglandins.

17 Claims, No Drawings

OXABICYCLOOCTANES AND PROCESS FOR THEIR MANUFACTURE

The present invention relates to new oxabicyclooctane derivatives and to a process for their manufacture. The new compounds are valuable intermediate products for the manufacture of biologically highly potent prostaglandins by a new, sterically controlled method process.

The invention relates in particular to new 2-oxabicyclo[3,3,0]octane derivatives of the formula IX,

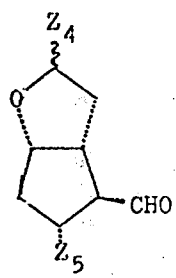
(IX)

wherein $Z_4$ and $Z_5$ each independently represent free, etherified or esterified hydroxy groups, and the optical antipodes and racemates thereof, and to a method process for their manufacture.

The significance of the present invention resides in the manufacture from readily accessible and inexpensive starting materials of intermediate products which can be used for the stereospecific synthesis both of known, naturally occurring prostaglandins as well as of new synthetic prostaglandins. The individual steps proceed with high yields. The new intermediate products are therefore suitable for carrying out the synthesis of the cited prostaglandins on an industrial scale.

From these intermediate products it is possible to manufacture first and foremost the prostaglandins of the $F_\alpha$-series which are characterised by an optionally unsaturated α-alkanecarboxylic acid in 8-position, an α-hydroxyolefine grouping in 12-position and two α-hydroxy groups in 9,11-position. Secondly, it is possible to use the new compounds as intermediate products for the manufacture of prostaglandins of the E, A and B series, and furthermore of derivatives and homologs of prostaglandins.

The biological activity and the importance of prostaglandins in medicine are known and described, for example, by M. P. L. Caton in *Progr. Med. Chem.* 8, 317 (1971).

The standard prostaglandin numbering used herein is derived from prostanoic acid which has the following structure:

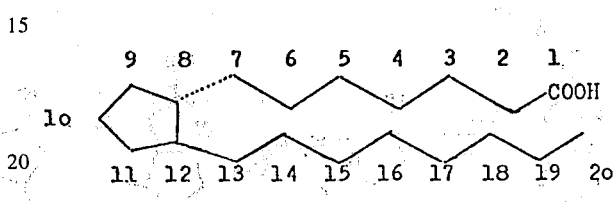

In the above formulae, as well as in those hereinafter, dotted lines indicate substituents which are situated behind the plane defined by the cyclopentane ring; these substituents are denoted by α. Thickly drawn lines indicate substituents which are in front of this plane; these are denoted by β. Substituents linked by wavy lines can be in the α- or β-configuration. The standard prostaglandin nomenclature is used as illustrated hereinabove in the formula of prostanoic acid. For the standard prostaglandin nomenclature compare also S. Bergström, *Science*, 157, 382 (1967), M. P. L. Caton, *Progr. Med. Chem.* 8, 317, (1971) and Niels Andersen, *Annals of the New York Academy of Sciences*, Vol. 180, S. 14, Apr. 30, 1971.

The stereospecific manufacture of the cited prostaglandins using the new compounds according to the invention is carried out by a new and original multi-step process. The following scheme reproduces, for example, the synthesis of natural prostaglandins $F_{2\alpha}$ (PGF$_{2\alpha}$) (XIIIa) and $F_{3\alpha}$ (PGF$_{3\alpha}$) (XIIIb).

Synthesis scheme

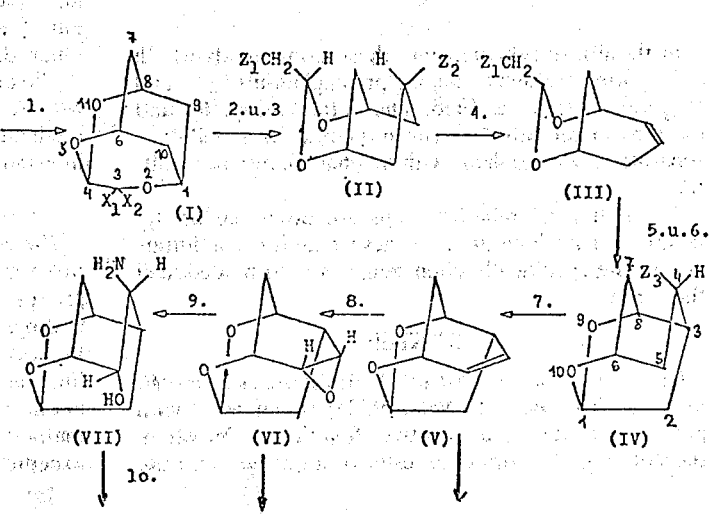

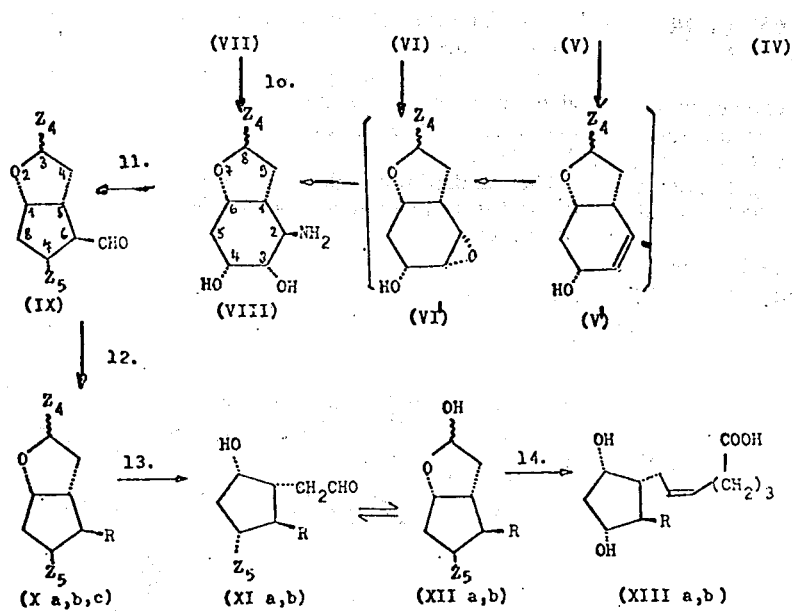

In the formulae X*a*, XI*a*, XII*a* and XIII*a*, R represents the group

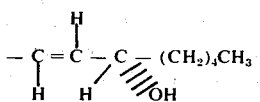

in the formulae X*b*, XI*b*, XII*b* and XIII*b*, R represents the group

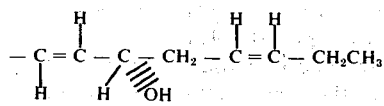

and in the formula X*c*, R represents the group

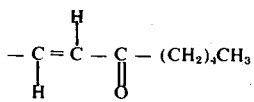

In the above scheme, only those compounds which lead to the naturally occurring prostaglandins $F_{2\alpha}$ and $F_{3\alpha}$ have been specified. The optical antipodes and diastereoisomers which occur in the reactions, and their separation, will be dealt with in what follows hereinafter.

The individual reaction steps are described briefly below, but no limitation to these reaction conditions and to the specifically cited reagents is to be deduced therefrom.

1ST STEP

Cis-cyclohexane-1,3,5-triol [K. H. Steinacker and H. Stetter, *Chem. Ber.* 85, 451 (1952)] is converted with glyoxylic acid, or a reactive functional derivative thereof, e.g. its hydrate, an ester or an acetal, into the compound of the formula I, in which $X_1$ and $X_2$ together represent the oxo group. The reaction is advantageously carried out in the presence of an acid catalyst, e.g. p-toluenesulphonic acid, in an inert solvent, e.g. benzene or ethylene glycol dimethyl ether, at a temperature of about 20°C to the boilling point of the solvent employed.

The compound of the formula I, in which $X_1$ represents a hydrogen atom and $X_2$ represents the hydroxy group, is formed when cis-cyclohexane-1,3,5-triol is reacted under similar conditions with glyoxal, or a reactive functional derivative thereof, e.g. the hydrate or one of its acetals.

2ND STEP

A compound of the formula I is converted by reduction into a compound of the formula II, wherein $Z_1$ and $Z_2$ are hydroxy groups. Complex hydrides, e.g. lithium aluminum hydride, lithium borohydride or sodium borohydride, can be used as reducing agents. The reduction is carried out at reduced or slightly elevated temperature, preferably between about 10°C and 100°C, in a suitable solvent. Lithium aluminum hydride or lithium borohydride are preferably used in ethereal liquids, such as diethyl ether, ethylene glycol dimethyl ether, dietylene glycol dimethyl ether, tetrahydrofuran or dioxan. It is also possible to carry out the reduction with sodium borohydride in lower alkanols, such as methanol, ethanol, isopropanol or tert. butanol, or also in water.

3RD STEP

The compound falling under the formula II manufactured in the 2nd. step, in which $Z_1$ and $Z_2$ are hydroxy groups, is converted with methanesulphonyl chloride and pyridine into its dimesylate, which also falls under the formula II. The reaction can be carried out in pyridine as solvent and maintaining low temperatures, about −20°C. According to another esterification method, it is possible to use triethylamine as proton acceptor and methylene chloride as solvent.

4TH STEP

The compound of the formula II, wherein $Z_1$ and $Z_2$ represent esterified hydroxy groups, e.g. mesyloxy groups, is converted into the compound of the formula III, in which $Z_1$ has the same meaning as in the starting material, by splitting off $H-Z_2$ with a base to form the double bond. Organic or inorganic bases can be used as bases. Particularly suitable bases are 1,5-diazabicyclo [5,4,0]undec-5-ene, which can be used in e.g. dimethyl sulphoxide at a temperature of about 110°C, or tetra-n-butylammonium fluoride, which can be used e.g. in dimethyl formamide at a temperature of about 60°C. Particularly preferred are alkali hydroxides, such as potassium hydroxide, e.g. in lower alkanols, such as isopropanol, at elevated, e.g. reflux, temperature.

In the reaction according to this step the racemate is formed, which can be used as such in the next step. If desired, the racemate can be resolved into both its optical antipodes by one of the methods described hereinafter.

5TH STEP

The bicyclic compound of the formula III, wherein $Z_1$ is for example a mesyloxy group, or the corresponding racemate, can be converted in surprising manner into the tricyclic compound of the formula IV, wherein $Z_3$ is a hydroxy group. This reaction is surprising because normally the formation of two six-membered rings, but not of a five-membered and a seven-membered ring, would be expected.

The reaction is preferably carried out in a water-miscible solvent, e.g. in ethylene glycol dimethyl ether/water mixture, in the presence of potassium carbonate at a temperature of about 80°C.

The reactions of the 4th and 5th steps can also be carried out in one operation by treating a diester falling under the formula II, e.g. dimesylate, with a solution of hydroxyl ions, e.g. with an alkali solution, such as a potassium hydroxide solution, in a solvent, such as in a lower alkanol, e.g. isopropanol. If desired, the crude compound of the formula IV, or its racemate, can be purified via its acetate.

If a antipodes. is made from the racemit mixture, consisting of the compound of the formula III and its optical antipode, there is obtained the racemit mixture consisting of the compound of the formula IV and its optical atipodes. The separation into the antipodes can also be effected in this step as described further on. However, instead of starting from the racemate, it is also possible to start from the optically active compound of the formula III, in the process of which the optically active compound of the formula IV is obtained directly.

6TH STEP

The secondary alcohol of the formula IV, wherein $z_3$ is a hydroxy group, or its racemate, is converted in the usual manner with methanesulphonyl chloride and a suitable base, e.g. triethylamine or pyridine, in a suitable solvent, e.g. in methylene chloride, into the compound of the formula IV, in which $Z_3$ represents the mesyloxy group. If desired, it is also possible in this step to effect the resolution into the optical antipodes, as described later in more detail.

7TH STEP

The methylsulphonyl ester of the formula IV, or its racemate, is converted into the unsaturated compound of the formula V, or its racemate, by splitting off methanesulphonic acid. The splitting off is effected in the presence of a base, e.g. potassium tert. butylate, or 1,5-diazabicyclo [5,4,0]undec-5-ene, in a solvent, e.g. dimethyl sulphoxide, or, preferably, in the presence of an alkali hydroxide, such as potassium hydroxide, in a boiling lower alkanol, such as isopropanol.

8TH STEP

The unsaturated compound of the formula V, or its racemate, is oxidised with e.g. a hydroperoxide, for example, a peracid, such as m-chloroperbenzoic acid, or, preferably, with a peroxyimidic acid, for example peroxybenzimidic acid, to a mixture consisting of the $\alpha$-epoxide of the formula VI and the corresponding $\beta$-epoxide, or the racemates thereof, preferably at slightly elevated temperature or elevated temperature, e.g. between about 0°C and 50°C. When using a peracid, such as m-chloroperbenzoic acid, the $\beta$-epoxide is formed as main product; when using a peroxyimidic acid, such as peroxybenzimidic acid, which can be prepared from an optionally substituted benzonitrile or lower alkyl nitrile with hydrogen peroxide in the presence of a base, such as an alkali metal bicarbonate, e.g. potassium bicarbonate, in a solvent, such as a lower alkanol, e.g. in methanol, surprisingly more $\alpha$- than $\beta$-epoxide is obtained. Both epoxides can be separated, for example, by chromatography, or further processed as a mixture. The separated $\beta$-epoxide, or its racemate, can be reduced with a complex hydride, e.g. with lithium aluminium hydride, in a solvent, e.g. in tetrahydrofuran, to an alcohol of the formula IV, or its racemate. The $\beta$-epoxide is thereby led back into the process. In this step it is also possible to perform any desired racemate separation.

9TH STEP

In an $\alpha$-epoxide of the formula VI, or its racemate, it is possible to open the epoxide ring, for example, with ammonia in a solvent, such as water, at elevated temperature, e.g. between about 50°C and 150°C, optionally under pressure, in the process of which a compound of the formula VII, its racemate or acid addition salts thereof, are formed. The epoxide ring is opened in such a way that the 4$\beta$-amino-5$\alpha$-hydroxy compound of the formula VII, or its racemate, is formed. The possible isomeric 5$\beta$-amino-4$\alpha$-hydroxy compound is not obtained, or is obtained in undetectably small amounts. If desired, it is possible to resolve an optionally resulting racemate.

10TH STEP

A compound of the formula VII, its racemate or an acid addition salt thereof, can be converted in the presence of a lower alkanol, such as methanol, by treatment with an acid, for example a hydrohalic acid, e.g. hydrochloric acid, into a compound of the formula VIII, wherein $Z_4$ represents lower alkoxy, e.g. methoxy, its racemate or an acid addition salt thereof. The reaction can be carried out at slightly reduced or elevated temperature, e.g. between about 0° and 50°C. It is also possible here to resolve an optionally resulting racemate.

Steps 8–10, i.e. the epoxidation of an olefine, amininolysis of the epoxide and splitting of the 6–10 bond in the tricyclic skeleton, can also be carried out in another sequence. For example, in an α-epoxide of the formula VI, or its racemate, the 6–10 bond can be split according to the reaction conditions of the 10th. step, and in the resulting 2,3-endoepoxy-4-endo-hydroxy-8-alkoxy-7-oxabicyclo[4,3,0]nonane of the formula VI', or in the racemate thereof, the epoxy grouping can be aminolysed according to the method of the 9th step, in the process of which a compound of the formula VIII, or its racemate, is formed, Furthermore, in a tricyclic olefine of the formula V, or in its racemate, it is possible to cleave the 6–10 bond according to the reaction conditions of the 10th step and, in the resulting bicyclic olefine of the formula V', or in its racemate, to epoxidise the double bond according to the method of the 8th step, whereupon once again a compound of the formula VI', or its racemate, is obtained.

11TH STEP

From the compound of the formula VIII, its racemate or an acid addition salt thereof, it is possible to split off the amino group, in the process of which a ring contraction simultaneously takes place and an aldehyde of the formula IX, wherein $Z_4$ is lower alkoxy, such as methoxy, and $Z_5$ is hydroxy, or its racemate, is formed. The splitting off can be performed by diazotisation, e.g. with nitrous acid, prepared in situ from one of its salts, such as sodium nitrite, and an acid, such as acetic acid, or with an anhydride of nitrous acid, such as dinitrogen tetroxide, in a solvent, such as water, or in an ethereal solvent, such as ethylene glycol monomethyl ether, preferably at reduced temperature, e.g. between about −10° and +50°C. If desired, it is also possible to resolve an optionally obtained racemate by one of the methods described later herein, into both its optical antipodes.

12TH STEP

The aldehyde of the formula IX, wherein $Z_4$ represents methoxy and $Z_5$ represents hydroxy, or its racemate, can be used for the synthesis of primary steps which lead either to prostaglandin $F_{2\alpha}$ or also to $F_{3\alpha}$. The compound of the formula Xa can be manufactured therefrom by reaction with the Wittig reagent which is prepared in the conventional manner from 2-(S)-hydroxy-n-heptyltriphenylphosphonium iodide and methyl lithium [E. J. Corey et al.., Ann. New York Acad.Sci. 180 33 (1971)]. The reaction takes place at temperatures between about −78°C and about −25°C in tetrahydrofuran or ethylene glycol dimethyl ether, in the process of which a transdouble bond is formed. The compound of the formula Xb can be manufactured therefrom in analogous manner by using the known Wittig reagent from cis-2-(S)-hydroxy-4-n-heptenyltriphenylphosphonium iodide [E. J. Corey et al.., J.Am. Chem. Soc. 93, 1490 (1971)].

If the racemate consisting of the compound of the formula VI and its optical antipodes is used as starting material, there is obtained an diastereoisomer mixture which, with the aid of physicochemical separating operations, can be separated or further processed as such.

If instead of 2-(S)-hydroxy-n-heptyl-triphenylphosphonium iodide there is used racemic 2-hydroxy-n-heptyl-triphenylphosphonium iodide or the corresponding heptenyl derivatives, once again a diastereoisomer mixture is obtained which likewise can either be further processed or separated by the aid of physicochemical separating operations. The same diastereoisomer mixture is obtained by using instead of the 2-hydroxy-heptyl- or 2-hydroxy-heptenylphosphonium compounds a corresponding 2-oxo-heptyl- or 2-oxo-heptenyl derivative, e.g. 1-triphenylphosphonium-2-heptanone-bromide or the 1-triphenyl-phosphoranylidene-2-heptanone prepared therefrom with sodium hydrogen carbonate [M. Miyano and C. R. Dorn, Tetrahedron Letters 1615 (1969)], and reducing the resulting ketones of the formula Xc with a complex hydride, such as sodium borohydride. The two racemates obtained thereby can again either be further processed as such or resolved into their respective two optical antipodes with optically active auxiliary products by methods later described herein.

13TH STEP

The cyclic acetals of the formulae Xa and Xb, wherein $Z_4$ represents e.g. methoxy and $Z_5$ represents hydroxy, their racemates or the corresponding diastereoisomer mixtures, are hydrolysed under acid conditions to the compound of the formula XIa or XIb or to their racemates.

These compounds can be in the form of the free aldehyde or in that of the cyclic hemiacetal of the formula XII. In using optically active starting material of the formula Xa or Xb, the trihydroxy compounds already contain all steric prerequisites for their conversion in the next step into the natural, optically active $PGF_{2\alpha}$ and $PGF_{3\alpha}$. If a start is made from the racemate of a compound of the formula Xa or Xb, the racemate is obtained which consists of a mixture of the compound of the formula XIa or XIb and the optical antipodes thereof. The separation of the racemate can be effected by one of the conventional processes later described herein. By starting from the diastereoisomer mixtures which may be obtained in the 12th step, once again diastereoisomer mixtures are obtained which can be further processed as such or resolved analogous to the methods mentioned in the 12th step.

14TH STEP

The compounds of the formula XIa or XIb, corresponding hemiacetals of the formula XIIa or XIIb or also the corresponding racemates or diastereoisomer mixtures, are finally converted with the Wittig reagent from 5-triphenylphosphonovaleric acid [E. J. Corey, T. K. Schaaf, W. Huber, U. Koelliker and N. M. Weinshenker, J. Amer. Chem. Soc. 92, 397 (1970) and 91,5675 (1969)] in dimethyl sulphoxide [R. Greenwald, M. Chaykowsky and E. J. Corey, J. Org. Chem. 28, 1128 (1963)] into the prostaglandin $F_{2\alpha}$ of the formula XIIIa or $F_{3\alpha}$ of the formula XIIIb. Preferably a cis-double bond is formed in this reaction.

The natural, optically active $PGF_{2\alpha}$ or $F_{3\alpha}$ is obtained directly by using optically active starting material of the formulae XIa or XIb, XIIa or XIIb. By starting from the racemate of the compound of the formula XIa or XIb or XIIa or XIIb, a racemate is obtained which consists of a mixture of natural $PGF_{2\alpha}$ and $PGF_{3\alpha}$ and the optical antipodes thereof. The racemate separation can be effected by one of the conventional methods later described herein.

If a start is made from the diastereoisomer mixtures which may be obtained in the 13th step, once again mixtures are obtained which consist of the naturally occurring prostaglandin $F_{2\alpha}$ and $F_{3\alpha}$ and their diastereoisomers, which can be used as such or resolved as mentioned in the 12th step.

The racemates mentioned hereinbefore can be resolved into their optical antipodes by methods which are known per se.

One of these methods consists in reacting a racemate with an optically active auxiliary substance, separating the resulting mixture of two diastereoisomer compounds with the aid of appropriate physicochemical methods and then resolving the individual diastereoisomeric compounds into the optically active starting materials.

Particularly suitable racemates for resolution into the antipodes are those which possess an acid group, e.g. the racemate of the compound of the formula XIII. It is possible to convert other described racemates into acid racemates by simple reactions. For example, the aldehydes of the formulae IX and XI react with a hydrazine derivative carrying an acid group, e.g. 4-(4-carboxyphenyl)-semicarbazide, to give the corresponding hydrazone derivatives, or the alcohols of the formulae IV, VIII or X react with a dicarboxylic anhydride e.g. phthalic anhydride, to give the racemate of an acid half ester.

These acid racemates can be reacted with optically active bases, e.g. esters of optically active aminoacids, or (−)-brucine, (+)-quinidine, (−)-quinine, (+)-quinquonine, (+)-dehydroabietylamine, (+)- and (−)-ephedrine, (+)-and (−)-1-phenyl-ethylamine or the N-mono- or dialkylated derivatives thereof, to give mixtures consisting of two diastereoisomeric salts.

The racemates cited hereinbefore which contain hydroxy groups can also be resolved into their optical antipodes, for which purpose there are used in particular optically active acids, or reactive functional derivatives thereof, which form diastereoisomeric esters with the cited alcohols. Examples of such acids are: (−)-abietic acid, D(+)-and L(−)-malic acid, N-acylated optically active aminoacids, (+) and (−)-camphanic acid, (+) and (−)-ketopinic acid, L(+)-ascorbic acid, (+)-camphoric acid, (+)-campher-10-sulphonic acid (β), (+) or (−)-α-bromo-camphor-π-sulphonic acid, (D(−)-quinic acid, (D(−)-isoascorbic acid, D(−)- and L(+)-mandelic acid, (+)-1-methoxyacetic acid, D(−)- and L(+)-tartaric acid and the di-O-benzoyl and di-O-p-toluyl derivatives thereof.

Racemates which contain hydroxy groups can be converted into a mixture of diastereoisomeric urethanes, for example by reaction with optically active isocyanates, such as (+)- or (−)-1-phenylethylisocyanate.

It is possible for basic racemates, such as those of the formulae VII and VIII, to form diastereoisomeric salts with the above cited acids.

Racemates which contain double bonds can be converted, for example with platinum chloride and (+)-1-phenyl-2-amino-propane, into mixtures of diastereoisomeric complex salts.

Physicochemical methods are suitable for separating the distereoisomeric mixtures, chiefly fractionated crystallisation. But chromatographic methods can also be used, primarily solid-liquid chromatography. Readily volatile diastereoisomeric mixtures can be separated also by distillation or gas chromatography.

The resolution of the separated diastereoisomeric compounds into the optically active starting materials is also performed by conventional methods.

The acids or bases are liberated from the salts, e.g. by treatment with acids or bases which are stronger than those originally used. From the esters and urethanes are obtained the desired optically active compounds, for example by alkaline hydrolysis or by reduction with a complex hydride, such as lithium aluminium hydride.

A further method of resolving the racemates consists in chromatography on optically active absorption layers, for example on cane sugar.

According to a third method, the racemates are dissolved in an optically active solvent and the more sparingly soluble optical antipode is crystallised out.

In a fourth method, the varying reactivity of the optical antipodes to biological material, such as microorganisms or isolated enzymes, is utilised.

In a fifth method, the racemates are dissolved and one of the optical antipodes is crystallised by inoculation with a small amount of an optically active product obtained by the above methods.

The term "lower" used to qualify the syllable "alk", e.g. in lower alkane, lower alkyl, lower alkoxy, lower alkylene and the like, indicates that the respective hydrocarbon radicals contain up to 7 carbon atoms, but in general up to 4 carbon atoms are preferred.

In the compounds of the present invention it is possible for a hydroxy group to be etherified e.g. by a substituted lower alkanol, for example a lower alkanol containing halogen or phenyl, such as 2-iodoethanol, trichloroethanol, benzyl alcohol, diphenyl methanol, triphenyl carbinol, 2-phenethyl alcohol, or preferably by a lower alkanol or a cycloalkanol with 5 to 7 carbon atoms, in which one of the methylene groups, in particular that in the α-position, can be replaced by a heteroatom, preferably by oxygen. Examples of these latter are methanol, ethanol, cyclopentanol, cyclohexanol, tetrahydropyran-2-ol and 1-lower alkoxy- lower alkanols, such as 1-methoxyethanol and 1-ethoxyethanol.

A hydroxy group can also be etherified with a tri-lower alkylsilyl, such as a trimethylsilyl or dimethyl tert. butylsilyl group.

In the compounds according to the invention, a hydroxy group can be esterified for example with a weak acid, such as an aliphatic monocarboxylic acid, preferably with a lower alkanecarboxylic acid, e.g. acetic acid, also with a lower alkanecarboxylic acid substituted e.g. by halogen, such as trifluoro- or trichloroacetic acid, with an aliphatic dicarboxylic acid, such as oxalic or malonic acid, with an aromatic carboxylic acid such as an optionally by alkyl, phenyl, nitro or halogen substituted benzoic acid, e.g. benzoic acid, p-methylbenzoic acid, p-biphenylcarboxylic acid, p-nitrobenzoic acid or p-chlorobenzoic acid, or also with an aromatic dicarboxylic acid, such as an optionally substituted benzene dicarboxylic acid e.g. phthalic acid.

In the preferred compounds of the formula IX and their racemates $Z_4$ represents a hydroxy group which is etherified with a lower alkanol and $Z_5$ represents a hydroxy group which is etherified with 1-methoxyethanol, 1-ethoxyethanol, tetrahydropyran-2-ol or with a tri-lower alkylsilyl group, or represents in particular a free hydroxy group.

It is possible to obtain a compound of the formula IX, or the optical antipode or racemate thereof, by diazotising the amino group in a compound of the formula VIII

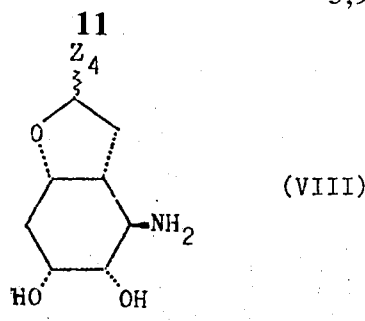

(VIII)

in which $Z_4$ has the meaning given under the formula IX, or the optical antipode or racemate or an acid addition salt thereof, eliminating the diazonium group accompanied by ring contraction, and, if desired, etherifying or esterifying a resulting compound of the formula IX, wherein $Z_5$ represents a hydroxy group, or the optical antipode or racemate thereof, and /or, if desired, resolving an optionally resulting racemate into the optical antipodes.

The diazotisation of the amino group can be carried out e.g. with nitrous acid or with a reactive functional derivative thereof, for example a salt thereof, such as an alkali metal salt, e.g. sodium nitrite. The process is carried out preferably in aqueous or aqueous-organic solution, for example in an aqueous lower alkanol, such as ethanol, usually in the presence of an acid, in particular of a lower alkanecarboxylic acid, such as acetic acid. It is also possible to carry out the diazotisation with an ester, such as a lower alkyl ester, or an anhydride of nitrous acid, e.g. amyl nitrite, dinitrogen trioxide or tetroxide, in an organic solvent, such as a lower alkanol, e.g. methanol, a lower alkanecarboxylic acid, e.g. acetic acid, an ester or amide thereof, such as ethyl acetate or dimethyl formamide, an ethereal liquid, such as a di-lower alkyl ether, e.g. diethyl ether, an optionally chlorinated hydrocarbon, such as chloroform or benzene. The reaction is preferably carried out at reduced or slightly elevated temperatures, e.g. between about −10° and +50° C. The splitting off of nitrogen from the diazonium compound formed as an intermediate and the ring contraction occur under the diazotisation conditions.

The etherification or esterification of a compound of the formula IX, or of the optical antipode or racemate thereof, with a free hydroxy group $Z_5$, can be carried out in known manner. Such a hydroxy compound is etherified by reacting it with e.g. an alcohol or with a reactive ester of an alcohol, e.g. of a lower alkanol which is optionally substituted by halogen or phenyl.

Reactive esters of such alcohols are, for example, those with strong acids such as hydrohalic acids, for example hydroiodic or hydrobromic acid, or with strong organic, e.g. aliphatic or aromatic, sulphonic acids, such as lower alkanesulphonic acids which are optionally substituted by halogen, e.g. methanesulphonic acid, or benzenesulphonic acids which are optionally substituted by e.g. lower alkyl, such as methyl, phenyl, nitro or halogen, such as chlorine or bromine, for example benzenesulphonic acid, p-toluenesulphonic acid or p-bromobenzenesulphonic acid.

The etherification is preferably carried out in the presence of a base, e.g. of a strong organic nitrogen base, e.g. a tert.lower alkyl amine, such as ethyl diisopropylamine, advantageously in the presence of an organic solvent, e.g. of an ethereal liquid, such as a di-lower alkyl ether, e.g. diethyl ether, an ethylene glycol di-lower alkyl ether, such as ethylene glycol dimethyl ether, or a cyclic ether, such as tetrahydrofuran or dioxan, of a hydrocarbon, such as benzene or toluene, or a di-lower alkyl amide of a lower alkanecarboxylic acid, such as dimethyl formamide or dimethyl acetamide.

It is possible to manufacture a compound of the formula IX, or the racemate thereof, which is etherified with a lower alkanol or cycloalkanol with 5 to 7 carbon atoms, wherein one of the methylene groups, in particular one in the α-position, is replaced by a heteroatom, such as oxygen, for example with 1-methoxyethanol, 1-ethoxyethanol or tetrahydropyran-2-ol, from a hydroxy compound of the formula IX, or the racemate thereof, with the aid of a corresponding olefin, e.g. methyl vinyl ether, ethyl vinyl ether or 2,3- dihydropyran, and by treatment with an acid, such as a Lewis acid, e.g. boron trifluoride, or with a mineral acid, such as hydrohalic acid or sulphuric acid. The process is preferably carried out in a solvent, such as an ethereal liquid, e.g. a lower alkyl ether, such as diethyl ether, or in an optionally chlorinated hydrocarbon, such as benzene or methylene chloride.

Hydroxy compounds of the present invention which are etherified with tri-lower alkyl-silyl, such as trimethyl- or dimethyl-t.butylsilyl groups, can be manufactured by treating the corresponding hydroxy compounds with a suitable silylating agent, such as trimethylchlorosilane, dimethyl-t.butyl-chlorosilane, hexamethyldisilazane, trimethylsilylamine, trimethylsilyl diethylamine, trimethylsilylimidazole, N-trimethylsilylacetamide or also bis-(trimethylsilyl)-acetamide, in an anhydrous solvent, such as dimethyl formamide, dimethyl sulphoxide or acetonitrile, optionally in the presence of an anhydrous base, such as triethylamine, piperidine, pyridine or imidazole.

In resulting hydroxy compounds, e.g. compounds of the formula IX and racemates, wherein the group $Z_5$ represents a free hydroxy group, it is possible to convert this group by esterification into an esterified hydroxy group, for example by reaction with the acids cited in the definition of these groups, preferably in the presence of agents which split off water, such as alkyl- or cycloalkylcarodiimides, e.g. dicyclohexylcarbodiimide, or diimidazolcarbonyl, or preferably with reactive derivatives of these acids, e.g. anhydrides, for example a lower alkanecarboxylic anhydride, such as acetic anhydride, including a mixed anhydride, for example with a carbonic acid lower alkyl half-ester, such as the ethyl half-ester of carbonic acid, halides, such as chlorides, for example an optionally substituted benzoyl chloride, such as p-phenylbenzoyl chloride, activated esters, such as phenyl esters which are substituted by one or more nitro groups, e.g. p-nitrophenyl ester. The esterification with such acid derivatives is carried out preferably in the presence of a base, e.g. of an alkali salt of a weak acid, such as carbonic acid, for example potassium carbonate, of an amine, for example of a tri-lower alkyl-amine, e.g. triethylamine, or, preferably, of a nitrogen-containing heterocyclic base, e.g. pyridine, alkylpyridine or quinoline.

The invention also comprises those embodiments of the process in which a start is made from compounds which are obtainable as intermediate products at any stage and the remaining steps of the process are carried out with these, or the process is discontinued at any stage; it is also possible to use starting materials in the form of derivatives or which are formed during the reaction.

Preferred starting materials and reaction conditions are those which lead to the compounds cited at the outset as being especially preferred.

The resolution of a racemate obtained according to the present invention can be effected in known manner by one of the methods described herein.

The starting materials required for the manufacture of the compounds of the present invention, i.e. the amine of the formula VIII and its optical antipode and racemate, are also new. They can be manufactured for example by solvolysing a compound of the formula VII

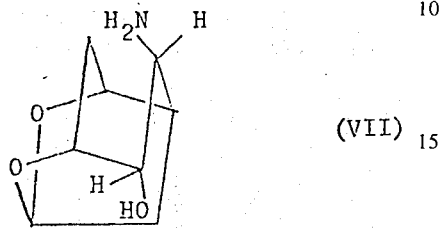

(VII)

or the optical antipode or racemate thereof, or an acid addition salt thereof, the manufacture of which has been described in the 9th step of the multi-step process exemplified at the outset, with a compound of the formula $Z_4H$, and, if desired, converting a resulting compound within the compass of the final products, and/or, if desired, resolving a resulting racemate into the optical antipodes.

For the solvolysis it is possible to use as compound of the formula $Z_4H$ water, one of the alcohols cited hereinabove, preferably a lower alkanol, such as methanol, or one of the acids cited hereinabove, preferably a lower alkanecarboxylic acid, such as acetic acid. The process is preferably carried out in the presence of an acid catalyst, such as a Lewis acid, e.g. of a halide of boron, aluminium, titanium, tin, phosphorus antimony or iron, preferably of boron trifluoride, or of a proton acid, e.g. a hydrohalic acid, such as hydrochloric acid, an oxyacid, such as sulphuric acid, a sulphonic acid, such as a lower alkane- or benzenesulphonic acid which is optionally substituted by e.g. halogen, alkyl or phenyl, such as methane- or toluene- sulphonic acid, also of an acid ion exchanger. As solvent there is used preferably an excess of the agent required for the solvolysis in the presence or absence of a diluent, such as an ethereal solvent, e.g. a di-lower alkyl ether or cyclic ether, such as dioxan. The reaction temperature can be reduced or slightly elevated, for example between about 0° and 50°C.

A resulting amine can be converted into an acid addition salt e.g. by reduction with an inorganic or organic acid or a corresponding anion exchanger and isolation of the salt which has been formed. A resulting acid addition salt can be converted into the free compound e.g. by treatment with a base, such as an alkali metal hydroxide, ammonia or a hydroxyl ion exchanger.

The following Examples illustrate the invention in more detail, but without being in any way limitative thereof.

EXAMPLE 1

A mixture of 1.056 g (8 mmols) of cis-cyclohexane-1,3,5-triol, 1.072 g (11.6 mmols) of glyoxylic monohydrate, 2.0 g (10.5 mmols) of p-toluenesulphonic monohydrate, 50 ml of benzene and 10 ml of water is boiled under reflux for 16 hours in a Dean-Stark steam trap. After the reaction solution has cooled, it is decanted off from a small amount of undissolved resin, washed with 20 ml of a solution which is saturated with sodium chloride and sodium bicarbonate, and with 35 ml of water. The combined washings are extracted with methylene chloride and the methylene chloride layer is combined with the benzene solution, dried over sodium sulphate and concentrated in a water jet vacuum. The residue is recrystallised from methylene chloride/ether to give 2,5,11-trioxatricyclo[4,3,1,1$^{4,8}$] undecan-3-one of the formula Ia

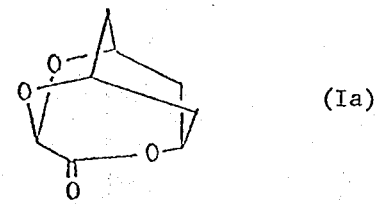

(Ia)

which melts at 140°–143°C.

EXAMPLE 1a

While stirring, 10.56 g (0.08 mols) of cis-cyclohexane-1,3,5-triol and 10.72 g (0.116 mols) of glyoxylic monohydrate in 400 ml of ethylene glycol dimethyl ether are heated until all is dissolved. To the cooled solution are added carefully 96 g of Amberlyst 15 (strongly acid catalyst in pearl form, Rohm and Haas Co.) [dried for 4 hours at 110°C and 0.05 Torr]. The resulting suspension is boiled under reflux for 30 minutes, cooled and filtered. The Amberlyst 15 which is filtered off is washed twice with 60 ml of ethylene glycol dimethyl ether each time and then with 1000 ml of methylene chloride. The filtrate is combined with the washings and extracted with 400 ml of normal sodium bicarbonate solution. The sodium bicarbonate solution is washed with 300 ml of methylene chloride, the methylene chloride solution is combined with the previously obtained organic solutiions and these are dried over sodium sulphate and evaporated in a water jet vacuum. The crystalline residue is recrystallised from methylene chloride/ether to give 2,5,11-trioxatricyclo[4,3,1,1$^{4,8}$]undecan-3-one of the formula Ia (m.p. 140°–143°C).

EXAMPLE 1b

A mixture of 500 mg (0.378 mmols) of cis-cyclohexane-1,3,5-triol and 920 mg (0.567 mmols) of methyl diethoxyacetate in 20 ml of ethylene glycol dimethyl ether is heated under reflux, treated after 15 minutes with 2 g of predried Amberlyst 15 (see Example 1a) and boiled for a further 10 hours under reflux with stirring. The catalyst is filtered off hot and washed twice with 20 ml of methylene chloride. The filtrate is concentrated under reduced pressure, the residue is taken up in the combined methylene chloride fractions and the resulting solution is shaken with 10 ml of water. The isolated aqueous layer is extracted with 10 ml of methylene chloride and the combined methylene chloride fractions are dried with anhydrous sodium sulphate and the solvent is distilled off. The crystalline residue is treated with 2 ml of ether and the crystalline 2,5,11-trioxatricyclo[4,3,1,1$^{4,8}$]undecan-3-one of the formula Ia is collected by suction filtration (m.p. 140°–143°C).

EXAMPLE 2 a. Analogous to Example 1, the 2,5,11-trioxatricyclo[4,3,1,1$^{4,8}$]undecan-3-ol of the formula Ib

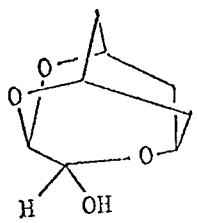

(Ib)

is obtained from the glyoxal hydrate and cis-cyclohexane-1,3,5-triol. Melting point: 185°–194°C.

b. To a stirred solution of 340 mg of 3,5,11-trioxatricyclo[4,3,1,1^{4,8}]undecan-3-one are added dropwise within 10 minutes under nitrogen and at room temperature, 2.8 ml of a 20% solution of diisobutylaluminium hydride in toluene. After a further 30 minutes at room temperature the reaction mixture is shaken with 0.8 ml of water and 2 g of silica gel for 15 minutes and, upon addition of 8 g of sodium sulphate, filtered through a glass filter. The filter cake is extracted ith a small amount of methylene chloride. The solvent is distilled off from the combined filtrates under reduced pressure to give pure 2,5,11-trioxatricyclo[4,3,1,1^{4,8}]undecan-3-ol of the formula Ib, which melts at 185°–194°C (sublimation at 145°C).

c. A solution of 340 mg of 2,5,11-trioxatricyclo[4,3,1,1^{4,8}]undecan-3-one in 10 ml of absolute ethanol is treated with 300 mg of sodium. After the metal has dissolved the reaction mixture is treated with 10 ml of water and 0.7 ml of acetic acid, concentrated under reduced pressure to about 3 ml and the concentrate is extracted with methylene chloride. The solvent is evaporated to leave as residue pure 2,5,11-trioxatricyclo-[4,3,1,1^{4,8}]undecan-3-ol.

EXAMPLE 3

A solution of 8.50 g (0.05 mols) of 2,5,11-trioxatricyclo[4,3,1,1^{4,8}]undecan-3-one of the formula Ia in 90 ml of ethylene glycol dimethyl ether is added dropwise within 15 minutes, while stirring and cooling with ice, to a suspension of 2.0g (0.05 mols) of lithium aluminium hydride in 60 ml of ethylene glycol dimethyl ether. The reaction mixture is boiled for 15 minutes under reflux, cooled to room temperature and carefully treated with 10 ml of ethyl acetate to destroy excess lithium aliminium hydride. Then, while stirring, 2.0 ml of water, 2.0 ml of 15% sodium hydroxide solution, and finally, 6 ml of water, are added to the reaction mixture. The precipitated salts are filtered off, stirred with 100 ml of methylene chloride and filtered again. The combined filtrates are concentrated in a water jet vacuum. The crystalline residue is recrystallised from methylene chloride to give 3-hydroxymethyl-2,4-dioxabicyclo[3,3,1]nonan-7-ol of the formula IIa

(IIa)

m.p. 149°–151°C.

EXAMPLE 3a

A solution of 340 mg of 2,5,11-trioxatricyclo[4,3,1,1^{4,8}]undecan-3-one of the formula Ia in 10 ml of absolute ethanol is treated at room temperature with 150 mg of sodium borohydride and the mixture is stirred for 2 hours. The reaction mixture is diluted with 10 ml of water, the pH adjusted to 8 with a few drops of glacial acetic acid and the resulting solution is concentrated under reduced pressure to about 3 ml. The concentrate is extracted three times with altogether 100 ml of methylene chloride, the combined extracts are dried with sodium sulphate and the solvent is distilled off to give 3-hydroxymethyl-2,4-dioxabicyclo[3,3,1]nonan-7-ol of the formula IIa, which melts at 146°–149°C.

EXAMPLE 3b

A similar 3 hour reduction of 340 mg of 2,5,11-trioxatricyclo[4,3,1,1^{4,8}]undecan-3-one of the formula Ia in 10 ml of isopropanol with 150 mg of sodium borohydride at 50°C, and subsequent working up as described hereinabove, leads to the same compound of the formula IIa.

EXAMPLE 3c

To a solution of 340 mg (2mmols) of 2,5,11-trioxatricyclo[4,3,1,1^{4,8}]undecan-3-one in 10 ml of methanol are added all at once 150 mg of sodium borohydride while stirring and cooling to 12°–15°C(water bath). After 1½ hours, during which time the bath temperature is allowed to rise to 20°C, a further 150 mg of sodium borohydride are added and the mixture is stirred for 2½ hours at 20°C. The reaction mixture is then treated with 10 ml of water, the pH adjusted to 8 with a few drops of acetic acid, and concentrated under reduced pressure to about 3 ml. The concentrate is extracted three times with 25 ml of methylene chloride on each occasion, the combined extracts are dried over sodium sulphate and the solvent is distilled off (at the conclusion under reduced pressure) to give crystalline 3-hydroxymethyl-2,4-dioxabicyclo[3,3,1]nonan-7-ol of the formula IIa (m.p.146°–149°C).

EXAMPLE 4

A solution of 0.87 g (5 mmols) of 3-hydroxymethyl-2,4-dioxabicyclo[3,3,1]nonan-7-ol of the formula IIa in 5 ml of anhydrous pyridine is cooled to −20°C and, while stirring, treated with 1,1 ml (14,2 mmols) of methanesulphonyl chloride. The cooling bath is removed and the reaction mixture is added after 1¼ hours to 40 ml of a normal sodium bicarbonate solution. The resulting mixture is extracted successively with 40 ml of ethyl acetate and 40 ml of methylene chloride. The combined organic solutions are washed with 10 ml of sodium bicarbonate solution, dried over magnesium sulphate and concentrated in a water jet vacuum. The crude product is recrystallised from acetone/heptane and gives 7-methylsulphonyloxy-3-methylsulphonyloxymethyl-2,4-dioxabicyclo[3,3,1]nonane of the formula IIb

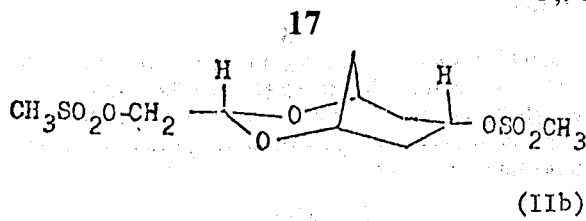

(IIb)

m.p. 137°–138°C.

EXAMPLE 5

To a solution of 348 mg (2 mmols) of 3-hydroxymethyl-2,4-dioxabicyclo[3,3,1]nonan-7-ol of the formula IIa in 2.0 ml of absolute pyridine are added at −15°C with stirring 1.28 g of p-bromobenzenesulphochloride all at once and the resulting mixture is further stirred under nitrogen for 48 hours at room temperature. The reaction mixture is treated with 25 ml of methylene chloride and shaken succesively with 15 ml of 8% NaHCO₃ and 15 ml of sodium chloride solution. The aqueous layers are extracted once more with methylene chloride. The combined organic phases are dried over sodium sulphate and freed from solvent and pyridine in a water jet vacuum and finally in an oil pump, to leave as residue crude 7-(p-bromophenylsulphonyloxy)-3-(p-bromophenylsulphonyloxymethyl)-2,4-dioxabicyclo [3,3,1]nonane of the formula IIc

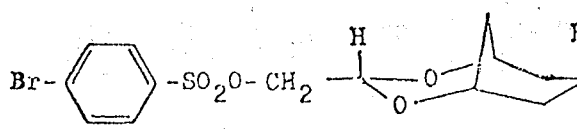

which congeals to a crystalline solid on standing. It is crystallised from boiling benzene with the addition of a small amount of hexane. Melting point: 128°C; the crystals contain ⅔ mols of benzene.

EXAMPLE 6

A solution of 1.65 g (5 mmols) of 7-methylsulphonyloxy-3-methylsulphonyloxymethyl-2,4-dioxabicyclo[3,3,1]nonane of the formula IIb and 3.0 ml (20 mmols) of 1,5-diazabicyclo[5,4,0]undec-5-ene in 25 ml of anhydrous dimethyl sulphoxide is heated for 45 minutes to 110°C. The reaction mixture is cooled to room temperature and then diluted with 150 ml of ether. It is then washed successively with 75 ml of 2n hydrochloric acid, 100 ml of water and finally with 100 ml of normal sodium bicarbonate solution. The aqueous layers are extracted separately twice with 150 ml of ether on each occasion. The last ethereal extract is washed with 50 ml of water and each organic extract is finally washed with 50 ml of concentrated sodium chloride solution. The organic solutions are dried over magnesium sulphate and evaporated in a water jet vacuum.

Chromatography of the residue on basic aluminium oxide (activity level IV) with benzene as eluant results in a racemic mixture of 3-methylsulphonyloxymethyl-2,4-dioxabicyclo[3,3,1]non -6-ene of the formula IIIa

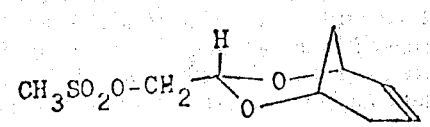

and its optical antipode, with a melting point of 54°–59°C.

EXAMPLE 6a

A solution of 660 mg of 7-methylsulphonyloxy-3-methylsulphonyloxymethyl-2,4-dioxabicyclo[3,3,1]nonane of the formula IIb and 1.4 g of tetrabutylammonium fluoride in 7.5 ml of dimethyl formamide is heated under nitrogen for 7 hours to 60°C. The cooled reaction mixture is treated with 20 ml of methylene chloride and 80 ml of ether and shaken successively with 80 ml of an 8% sodium bicarbonate solution, 100 ml of water and 50 ml of sodium chloride solution. The aqueous layers are extracted separately twice with 100 ml of the same solvent mixture on each occasion. The combined organic fractions are dried over sodium sulphate. The solvent is distilled off under reduced pressure to give an oily product whose spectrum properties correspond to those of the pure racemic 3-methylsulphonyloxymethyl-2,4-dioxabicyclo[3,3,1]non-6-ene of the formula IIIa. Preparative chromatography on basic aluminium oxide with benzene as eluant gives the crystalline product of melting point 53°–56° C.

EXAMPLE 6b

A mixture of 300 mg (0.91 mmols) of 7-methylsulphonyloxy- 3-Methylsulphonyloxymethyl-2,4-dioxabicyclo[3,3,1]nonane of the formula IIb and 15 ml of anhydrous toluene is heated to 80°C and treated within 2 hours in 5 amounts of altogether 300 mg of potassium tert.butylate dissolved in 5 ml of tert. butanol. The reaction mixture is stirred for a further 2 hours, then cooled, treated with saturated sodium chloride solution and extracted 5 times with 10 ml of methylene chloride on each occasion. The combined organic extracts are washed once more with saturated sodium chloride solution, dried over magnesium sulphate and concentrated. Preparative chromatography of the resulting residue on silica gel with ethyl acetate as eluant yields a racemic mixture consisting of 3-methylsulphonyloxymethyl-2,4-dioxabicyclo[3,3,1]non-6-ene of the formula IIIa and its optical antipode of melting point 50°–58°C.

EXAMPLE 6c

A solution of 60mg(0,18 mmoles)of 7-methylsulphonyloxy-3-methylsulphonyloxymethyl-2,4-dioxabicyclo[3,3,1]nonane of the formula IIb in 3 ml of ethylene glycol dimethyl ether (filtered through basic aluminium oxide) is heated to 80°C and treated with a solution of 60 mg (0.54 mmols) of sublimed potassium tert. butylate in 0.7 ml of tert. butanol. The reaction mixture is cooled after 4 hours, treated with a saturated sodium chloride solution and extracted 5 times with 6 ml of methylene chloride on each occasion. The organic phases are dried over magnesium sulphate, and the solvent is evaporated. Preparative layer chromatography on silica gel with ethyl acetate as eluant yields a racemic mixture consisting of 3-methylsulphonyloxymethyl-2,4-dioxabicyclo[3,3,1]non-6-ene and its optical antipode.

EXAMPLE 6d

A solution of 80mg(0,24 mmoles)7-methylsulphonyloxy-3-methylsulphonyloxy-methyl-2,4-dioxabicyclo[3,3,1]nonane of the formula IIb in 2 ml of dimethyl sulphoxide (which has been dried over calcium hydride) is treated dropwise within 10 minutes with a solution of 100 mg of potassium tert. butylate (0.89 mmols) in 3 ml of dimethyl sulphoxide. The reaction temperature is kept at 15°C. The reaction mixture is then diluted with 10 ml of ether and washed with 8 ml of 0.5 n hydrochloric acid and 10 ml of saturated sodium bicarbonate solution. The aqueous layers are extracted twice with 10 ml of ether on each occasion. The combined organic phases are washed again with 5 ml of sodium bicarbonate solution and 10 ml of water, dried over magnesium sulphate and concentrated in vacuo to give a racemic mixture consisting of 3-methylsulphonyloxymethyl-2,4-dioxabicyclo[3,3,1]non-6-ene of formula IIIa and its optical antipode.

EXAMPLE 6e

A solution of 100 mg (0.3 mmols) of 7-methylsulphonyloxy-3-methylsulphonyloxymethyl-2,4-dioxabicyclo[3,3,1]nonane of the formula IIb in 5ml of tert. butanol (distilled over calcium hydride) is heated to 80°C and 60 mg (0.54 mmols) of sublimed potassium tert.butylate dissolved in 2 ml of tert.butanol are added within 1 hour. The reaction mixture is heated for 6 hours at the same temperature, and then a further 11.0 mg. (0.1 mmols) of potassium tert. butylate, dissolved in 0.5 ml of tert. butanol, are added. The reaction mixture is heated for a further hour, cooled, treated with 40 ml of ether and washed 5 times with 15 ml of water each time. The organic phase is dried over magnesium sulphate and evaporated to give a racemic mixture consisting of 3-methylsulphonyloxymethyl-2,4-dioxabicyclo[3,3,1]non-6-ene of the formula IIIa and its optical antipodes, in the form of a colourless oil which crystallises on standing and is sufficiently pure for use in the following reaction.

EXAMPLE 6f

7-Methylsulphonyloxy-3-methylsulphonyloxymethyl-2,4-dioxabicyclo[3,3,1]nonane (280 mg) is added to 5 ml of a boiling 2n potassium hydroxide solution in absolute alcohol and the mixture is boiled for 2 minutes under reflux while stirring vigorously. The reaction mixture which has congealed to a crystalline solid is cooled and, after treatment with 5 ml of 8% sodium bicarbonate solution, extracted three times with methylene chloride. The combined extracts are dried with sodium sulphate and the solvent is distilled off under reduced pressure to leave as residue the crystalline racemic 3-methylsulphonyloxymethyl-2,4-dioxabicyclo[3,3,1]non-6-ene (m.p. 53°–56°).

EXAMPLE 6g

To a hot suspension of 280 mg of 7-methylsulphonyloxy-3-methylsulphonyloxymethyl-2,4-dioxabicyclo[3,3,1]nonane in 2,5 ml of isopropanol is added 2,5 ml of a boiling 2n potassium hydroxide solution in isopropanol while stirring vigorously, and the resulting reaction mixture is boiled under reflux for 3 minutes. The reaction mixture is cooled and treated with 5 ml of an 8% sodium bicarbonate solution, then extracted 3 times with methylene chloride. The combined extracts are dried over sodium sulphate and the solvent is distilled off in vacuo uner reduced pressure to leave as residue the racemic 3-methylsulphonyloxymethyl-2,4-dioxabicyclo[3,3,1]non-6-ene in the form of a colourless oil, which soon congeals to a crystalline solid (m.p. 53°–56°C).

EXAMPLE 7

A solution of 61mg of 7-(p-bromophenylsulphonyloxy)-3-(p-bromophenylsulphonyloxymethyl)-2,4-dioxabicyclo[3,3,1]nonane of the formula IIc and 220 mg of tetra-n-butylammonium fluoride in 1.0 ml of anhydrous dimethyl formamide is heated with stirring in a nitrogen atmosphere for 45 minutes to 60°C. The cooled reaction mixture is treated with 5 ml of methylene chloride and 25 ml of ether and shaken succesively with 8 ml of normal sodium bicarbonate solution, 10 ml of water and 10 ml of sodium chloride solution. The aqueous phases are extracted twice with 10 ml of the same solvent mixture on each occasion. All organic phases are dried together over sodium sulphate. The solvent is distilled off under reduced pressure to yield a racemic mixture consisting of 3-(p-bromophenylsulphonyloxymethyl)-2,4-dioxabicyclo[3,3,1]non-6-ene of the formula IIIb $$Br-\bigcirc-SO_2O-CH_2-\overset{H}{\underset{O}{\diagdown}}O-\diagup \qquad (IIIb)$$

and its optical antipode; m.p. 114°–117°C.

EXAMPLE 8

A solution of 363 mg (1.55 mmols) of racemic 3-methylsulphonyloxymethyl-2,4-dioxabicyclo[3,3,1]-non-6-ene and 215 mg (1.55 mmols) of potassium carbonate in 3.6 ml of acetone and 18 ml of water is stirred in a nitrogen atmosphere for 18 hours under reflux. The cooled reaction mixture is extracted 3 times with 30 ml of methylene chloride on each occasion.

The combined methylene chloride layers are concentrated, the residue is taken up in ethyl acetate and filtered through a column of 10 g of basic aluminium oxide (activity level IV). Elution is performed with ethyl acetate. Concentration of the first 60 ml of eluate in a water jet vacuum yields a racemic mixture of 9,10-dioxatricyclo[4,3,1,0$^{3,8}$]decan-4$\beta$-ol of the formula IVa $$\text{(IVa)}$$

and its optical antipode, which melts after recrystallisation at 134°–142°C (210°–232°C, sealed capillary).

EXAMPLE 8a

A solution of 75 mg (0.32 mols) of racemic 3-methylsulphonyloxymethyl-2,4-dioxabicyclo[3,3,1]non-6-ene of the formula IIIa and 44 mg (0.32 mmols) of potassium carbonate in 0.5 ml of ethylene glycol dimethyl ether and 2.5 ml of water, is stirred for 18 hours under reflux in an oil bath which is kept at 100°C. The cooled reaction solution is diluted with water, saturated with NaCl and extracted 5 times with 10 ml of methylene chloride on each occasion. The combined extracts are dried over magnesium sulphate and concentrated. The residue is resolved by means of preparative layer chromatography (on silica gel, eluant: methylene chloride-/acetone 1:1). A racemic mixture of 9,10-dioxatricyclo[4,3,1,0$^{3,8}$]decan-4$\beta$-ol of the formula IV$a$ and its optical antipode is obtained.

EXAMPLE 8$b$

To a well stirred suspension of 16.5g (0.05 mols) of racemic 7-methylsulphonyloxy-3-methylsulphonyloxymethyl-2,4-dioxabicyclo[3,3,1]nonane in 125 ml of boiling isopropanol is added a hot solution of 14 g of potassium hydroxide (0.25 mol) in 125 ml of isopropanol in one amount. In a few seconds a clear solution temporarily forms from which, however, potassium mesylate soon begins to precipitate. After stirring vigorously for 3 minutes at the boiling temperature of the solvent, the reaction mixture — which in the meantime has congealed to a crystalline solid — is treated with a solution of 25 g of potassium bicarbonate in 1250 ml of water and about 250 ml are distilled off under reduced pressure from the resulting clear solution. The reaction mixture is then brought to the original volume by adding water and boiled under reflux for 16 hours in a nitrogen atmosphere. It is then cooled, saturated with sodium chloride and repeatedly extracted with methylene chloride. The combined extracts are dried over sodium sulphate and the solvent is distilled off under reduced pressure to give the crystalline racemic mixture of 9,10-dioxatricyclo[4,3,1,0$^{3,8}$]decan-4$\beta$-ol and its optical antipode. In similar manner it is also possible to use a 2$n$ solution of potassium hydroxide in ethanol or in water/ethylene glycol monomethyl ether (2:1) for the splitting off of the methanesulphonic acid. The product can be further used without purification or purified as follows via its acetate:

A solution of 1.46 g of the racemic 9,10-dioxatriclo [4,3,1,0$^{3,8}$]decan-4$\beta$-ol in 25 ml of pyridine and 8 ml of acetic anhydride is allowed to stand for 14 hours at room temperature and then evaporated in a high vacuum. The residue is recrystallised from diethyl ether to give the pure racemic 4$\beta$-acetoxy-9,10-dioxatricyclo[4,3,1,0$^{3,8}$]decane which melts at 97°–98°C.

A solution of 198 mg of the pure racemic 4$\beta$-acetoxy-9,10-dioxatricyclo[4,3,1,0$^{3,8}$]decane in 8 ml of ethanol and 2 ml of 2 $n$ aqueous potassium hydroxide is boiled under reflux for 1 hours in a nitrogen atmosphere. The ethanol is then distilled off in vacuo and the residue is extracted 4 times with 20 ml of methylene chloride on each occasion. The methylene chloride solutions are evaporated and the pure 9,10-dioxatricyclo[4,3,1,0$^{3,8}$]decan-4$\beta$-ol is obtained, which after recrystallisation from benzene/cyclohexane melts at 250°–256°C (sealed capillary).

EXAMPLE 8$c$

A solution of 1.56 g (10.0 mmols) of the pure racemic 9,10-dioxatricyclo[4,3,1,0$^{3,8}$]decan-4$\beta$-ol (purified via the acetate) in 15 ml of pyridine is treated, while stirring, with 2.50 g(12.5 mmols) of (S)-ketopinylchloride (prepared from S-ketopininc acid with thionyl chloride/pyridine. S-ketopinic acid is prepared from (+)-10-camphorsulphonic acid monohydrate analogous to the process described in *Organic Syntheses* 45, 14,55). The reaction mixture is stirred for 18 hours at room temperature and added to a mixture of 25 ml of saturated sodium carbonate solution and 25 ml of water. The mixture is extracted 3 times with 50 ml of methylene chloride on each occasion. The methylene chloride solution is treated with benzene, then evaporated in vacuo, and the residue recrystallised 4 times from ethyl acetate to give the pure 8S-4$\beta$-(S-ketopinyloxy)-9,10-dioxatricyclo[4,3,1,0$^{3,8}$]-decane, [$\alpha$]$_D$= −47° (c=1 in chloroform) which melts at 183° –185°C. The mother liquor contains the crude 8R-4$\beta$-(S-ketopinyloxy)-9,10-dioxatriclo[4,3,1,0$^{3,8}$]-decane which melts at 111°–114°C. A solution of 1.28 g (4.0 mmols) of the pure 8S-4$\beta$-(S-ketopinyloxy)-9,10-dioxatricyclo[4,3,1,0$^{3,8}$]decane and 8.0 ml of 2$n$ aqueous potassium hydroxide in 32 ml of ethanol is boiled under reflux for 15 hours in a nitrogen atmosphere. The solution is then cooled, the ethanol evaporated in vacuo, the residue treated with 5 ml of water and extracted 6 times with 50 ml of methylene chloride on each occasion. The combined methylene chloride layers are evaporated, and the residue is first sublimed at 110°C (0.02 Torr) and then recrystallised from benzene/cyclohexane. The pure 8S-9,10-dioxatricyclo[4,3,1,0$^{3,8}$]decan-4$\beta$-ol of the formula IV$a$ melts at 251°–256°C, [$\alpha$]$_D$= −147° (c = 1 in chloroform).

EXAMPLE 8$d$

A solution of 1.56 g (10.0 mmols) of the racemic 9,10-dioxatricyclo[4,3,1,0$^{3,8}$]decan-4$\beta$-ol (purified via the acetate) in 30 ml of dry benzene is boiled for 14 hours under reflux with 1 ml of triethylamine and 2.2 g (15 mmols) of (−)-1-phenyl-ethylisocyanate. After evaporation in vacuo and drying in a high vacuum at 50°C the residue is crystallised out from ethyl acetate/-hexane and recrystallised 5 times from benzene. The resulting pure urethane melts at 144°–145°C and has the following optical rotation: [$\alpha$]$_D$ = −32° (c = 1 in chloroform). This urethane (50 mg) is boiled under reflux with 1.0 ml of 2$n$ potassium hydroxide solution in ethanol. The mixture is then treated with water (10 ml) and concentrated to 5 ml. The solution is washed 3 times with 20 ml of pentane on each occasion, then concentrated to 1 ml and the concentrate is extracted 5 times with 20 ml of methylene chloride on each occasion. The combined methylene chloride solutions are filtered through cotton wool and evaporated. The residue, 8S-9,10-dioxatricyclo[4,3,1,0$^{3,8}$]decan-4$\beta$-ol, has the optical rotation [$\alpha$]$_D$ = −147° ( c = 1 in chloroform).

In analogous manner it is possible to obtain the 8R-9,10-dioxatricyclo[4,3,1,0$^{3,8}$]-decan-4$\beta$-ol with the optical rotation [$\alpha$]$_D$ = +147° (c = 1 in chloroform) from the pure racemic 9,10-dioxatricyclo[4,3,1,0$^{3,8}$]decan-4$\beta$-ol with the aid of (+)-1-phenyl-ethylisocyanate.

EXAMPLE 8$e$

A solution of 100 mg of the racemic 4$\beta$,5$\beta$-epoxy-9,10-dioxatricyclo[4,3,1,0$^{3,8}$] decane in 3ml of dry tetrahydrofuran is boiled under reflux for 14 hours with 200 mg of lithium aluminium hydride. The mixture is then cooled, 0.2 ml of water, 0.2 ml of 2$n$ sodium hydroxide solution and 0.6 ml of water are added and the resulting suspension is stirred for 1 hour at room temperature. It is then filtered with suction and the precipitate is washed 3 times with 15 ml of methylene chloride on each occasion. The organic solutions are evaporated to yield the pure racemic 9,10-dioxatricyclo[4,3,1,0³,⁸]decan-4β-ol.

EXAMPLE 9

While stirring, a solution of 0.24 ml of methanesulphonyl chloride in 5.0 ml of methylene chloride is added at a temperature of −10°C to a solution of 156 mg (1.00 mmols) of racemic 9,10-dioxatricyclo[4,3,1,0³,⁸]decan-4β-ol and 0.55 ml (4.00 mmols) of triethylamine in 5,0 ml of methylene chloride. After 40 minutes, during which time the cooling bath has warmed to 0°C, the reaction mixture is diluted with 25 ml of methylene chloride and washed with 10 ml of normal sodium bicarbonate solution. The sodium bicarbonate layer is washed with 10 ml of methylene chloride and this methylene chloride layer is combined with the previous methylene chloride solution, dried over sodium sulphate and concentrated in a water jet vacuum. The residue is taken up in a small amount of ethyl acetate and filtered through a column of 5 g of basic aluminium oxide (activity level IV). After elution with ethyl acetate and concentrating the first 50 ml of the eluate there is obtained as residue a crude racemic mixture of 4β-methylsulphonyloxy-9,10-dioxatricyclo[4,3,1,0³,⁸]decane of the formula IVb

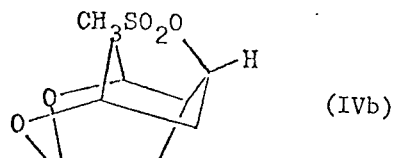

(IVb)

and its optical antipode, which can be used in the next reaction without further purification. However, it can also be recrystallised from ethyl acetate/pentane or ether/methylene chloride. Melting point: 102°–106°C. In analogous manner the 8S-4β-methylsulphonyloxy-9,10-dioxatricyclo[4,3,1,0³,⁸]decane of the formula IVb, which melts at 120°C (with decomp.) ethyl acetate/hexane,[α]_D = −90° (C = 1 in chloroform), is obtained from the 8S-9,10-dioxatricyclo[4,3,1,0³,⁸]decan-4β-ol.

EXAMPLE 9a

A solution of 550 mg (3.52 mmols) of the racemic 9,10-dioxatricyclo[4,3,1,0³,⁸]decan-4β-ol in 25 ml of ether (filtered over basic aluminium oxide) is treated with 900 mg of sodium hydride (50%) and the mixture is boiled under reflux for 3 hours. Then 2 ml of carbon disulphide are added and heating is continued for 3 hours. Finally, 2 ml of methyl iodide are added and the mixture is refluxed for a further 4 hours. The reaction mixture is cooled and excess sodium hydride is then destroyed with moist ether and subsequently with water. The organic phase is isolated and dried over magnesium sulphate. The solvent is expelled and the resulting oil is dissolved in benzene and filtered over aluminium oxide (activity level IV). After an extremely unpleasant smelling component has passed out of the column the eluate is combined and evaporated. Repeated crystallisation of the residue from heptane yields the racemic mixture consisting of 9,10-dioxatricyclo[4,3,1,0³,⁸]-decane-4β-methylxanthogenate of the formula IVc

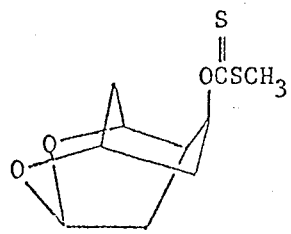

(IVc)

and its optical antipode; m.p. 81°–82°C.

EXAMPLE 10

A solution of the crude racemic 4β-methylsulphonyloxy-9,10-dioxatricyclo[4,3,1,0³,⁸]decane of the formula IVb, obtained in Example 9, in 1.0 ml of anhydrous dimethyl sulphoxide is treated in a nitrogen atmosphere and with stirring with 2.5 ml. of a freshly prepared normal solution of potassium tert.butylate in anhydrous dimethyl sulphoxide, and the mixture is stirred for 40 minutes. The reaction solution is then diluted with 50 ml of ether and washed 4 times with 10 ml of water on each occasion and once with 20 ml of saturated sodium chloride solution. The organic layer is concentrated, the residue taken up in a small amount of methylene chloride and the solution is filtered through a column of 2 g of basic aluminium oxide (activity level IV). After elution with methylene chloride and concentrating the first 50 ml of eluate in a water jet vacuum there is obtained as residue the racemc mixture of 9,10-dioxatricyclo[4,3,1,0³,⁸]dec-4-ene of the formula V

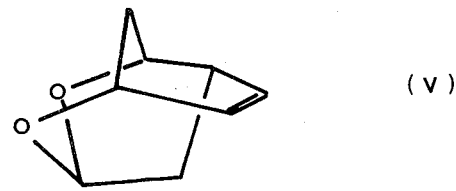

( V )

and its optical antipode, in the form of a wax-like substance; m.p. 103°–105°C. From 8S-4β-methylsulphonyloxy-9,10-dioxatricyclo[4,3,1,0³,⁸]decane there is obtained in analogous manner 8S-9,10-dioxatricyclo[4,3,1,0³,⁸]dec-4-ene, m.p. 108°–114°C; [α]_D = +11° (c = 1 in chloroform).

EXAMPLE 10a

To a boiling solution of 4.68 g of racemic 4β-methylsulphonyloxy-9,10-dioxatricyclo[4,3,1,0³,⁸]decane in 40 ml of isopropanol is added a hot solution of 4.48 g of potassium hydroxide in the same, solvent in a single amount and the resulting reaction mixtuure is refluxed for 2 hours with stirring. During this time the reaction mixture congeals to a crystalline solid from the precipitated potassium mesylate. It is then treated with 100ml of 8% sodium bicarbonate solution and repeatedly extracted with methylene chloride. The combined extracts are dried over sodium sulphate and evaporated under reduced pressure. The resulting crude product is dissolved in pentane/ether (9:1) and filtered through a column filled with 100 g of aluminium oxide (activity level IV). The first 500 ml of eluate yield after evaporation the racemic mixture of 9,10-dioxatricyclo[4,3,1,0$^{3,8}$]dec-4-ene of the formula V, and its optical antipode.

EXAMPLE 10b

To a solution of racemic 9,10-dioxatricyclo[4,3,1,0$^{3,8}$]-decane-4β-methylxanthogenate in methylene chloride is added the ten fold amount of sodium carbonate and the solvent is distilled off in a rotary evaporator. The resulting composition is heated to 150°C in a pyrolysis tube. The distillate which is collected contains the racemic 9,10-dioxatricyclo[4,3,1,0$^{3,8}$]dec-4-ene.

EXAMPLE 11

To a solution of 165 mg of racemic 9,10-dioxatricyclo[4,3,1,0$^{3,8}$]dec-4-ene in 4 ml of methanol are added, with stirring and at room temperture 865 mg of potassium bicarbonate and 750 mg of benzonitrile. To this mixture are added at intervals of 8 hours 5 positions each of 0.3 ml of 30% hydrogen peroxide and stirring is continued for 10 hours. methylene chloride (25 ml) is then added to the reaction mixture, which is washed with 2% sodium hydrogen carbonate solution, dried over sodium sulphate and concentrated, Benzamide which has formed is removed by crystallisation from methylene chloride/pentane. The residual oil can be used directly in the next reaction, or chromatographed on 22 g of basic aluminium oxide (activity level IV). Elution with petroleum ether/benzene (7:3) yields the racemic mixture of 4β, 5β-epoxy-9,10-dioxatricyclo[4,3,1,0$^{3,8}$]decane of the formula

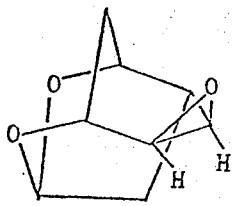

and its antipode, (m.p. after crystallisation from ether/pentane: 181°–182°C), and also as main product the racemic mixture of 4α,5α-epoxy-9,10-dioxatricyclo[4,3,1,0$^{3,8}$]decane of the formula

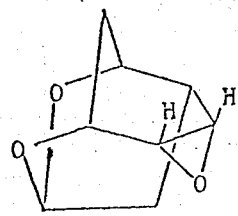

(VI)

and its antipode; (m.p. after crystallisation from ether/pentane: 146°–156°C).

From 8S-9,10-dioxatricyclo[4,3,1,0$^{3,8}$]dec-4-ene there is obtained in analogous manner the 8S-4α,5α-epoxy-9,10-dioxatricyclo[4,3,1,0$^{3,8}$]decane Melting point: 169°–171° [α]$_D$ = −95° (c= 1 in chloroform) and the 8S-4β,5β-epoxy-9,10-dioxatricyclo[4,3,1,0$^{3,8}$] decane. Melting point: 180°–182°, [α]$_D$ = −87° (c= 1 in chloroform).

EXAMPLE 11a

To a solution of 350 mg (2,53 mmols) of racemic 9,10-dioxatricyclo[4,3,1,0$^{3,8}$]dec-4-ene in 45 ml of chloroform (filtered through aluminium oxide of activity level I) are added 1.1 g (11 mmols) of finely powdered potassium bicarbonate and then, with stirring, 570 mg of 85% m-chloroperbenzoic acid (2.8 mmols). The mixture is stirred for 40 hours at room temperature, filtered and the filtrate is washed twice with 30 ml of a normal sodium carbonate solution on each occasion. The organic solution is filtered through cotton wool and evaporated. The residue is chromatographed on 20 g of basic aluminium oxide (activity level IV). The racemic 4β,5β-epoxy-9,10-dioxatricyclo[4,3,1,0$^{3,8}$]decane is eluted as main product with petroleum ether/benzene (7:3) and the racemic 4α,5α-9,10-dioxatricyclo[4,3,1,0$^{3,8}$]decane with benzene.

EXAMPLE 12

A solution of 800 mg (5.2 mmols) of racemic 4α,5α-epoxy-9,10-dioxaricyclo[4,3,1,0$^{3,8}$]decane in 35 ml of 24% aqueous ammonia is heated in a Carius tube under nitrogen for 1 hour at 100°C (bath temperature). Upon cooling, the contents of the tube are evaporated to dryness. The crystalline residue is taken up in methylene chloride. The solvent is evaporated to give the pure racemic mixture of 4β-amino-9,10-dioxatricyclo[4,3,1,0$^{3,8}$]decane-5α-ol of the formula

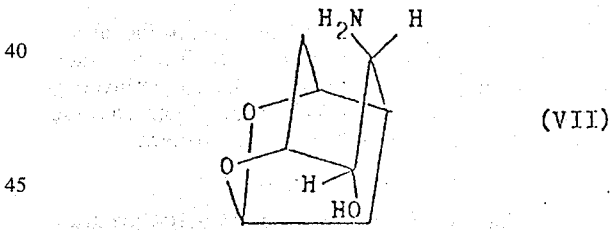

and its optical antipode, in the form of colourless crystals (m.p. 178°–180°C; sublimation at about 140°C).

In analogous manner there is obtained from the 8S-4α,5α-epoxy-9,10-dioxatricyclo[4,3,1,0$^{3,8}$]decane the 8S-4β-amino-9,10-dioxatricyclo[4,3,1,0$^{3,8}$]decan-5α-ol; m.p. 176°–178°,[α]$_D$ = −155° (c = 1 chloroform).

EXAMPLE 12a

A solution of 143 mg of the crude mixture of racemic 4α,5α-epoxy-9,10-dioxatricyclo[4,3,1,0$^{3,8}$]decane and the corresponding β-epoxide in 5 ml of 24% aqueous ammonia is heated in a Carius tube under nitrogen for 1 hour to 100°C (bath temperature). Upon cooling, the contents of the tube are evaporated to dryness in vacuo, the residue is dissolved in 5 ml of water, and this solution is washed twice with 10ml of diethyl ether on each occasion to remove unreacted β-epoxide. The aqueous phase is concentrated to yield the pure racemic 4β-amino-9,10-dioxatricyclo[4,3,1,0$^{3,8}$]-decan-5α-ol (m.p. 178°–180°C).

EXAMPLE 13

The racemic 4β-amino-9,10-dioxatricyclo[4,3,1,0³,⁸]-decan-5α-ol (400mg, 2.34 mmols) is dissolved in 18 ml of a 1.23% solution of hydrochloric acid in methanol and the solution is stirred under nitrogen for 2½ hours at room temperature. During this time the racemic 2-exo-amino-3,4-endo-dihydroxy-8-methoxy-7-oxabicyclo[4,3,0]nonane hydrochloride begins to crystallise from the reaction solution. The resulting suspension is evvaporated to dryness in vacuo and the white crystalline residue is freed from excess hydrogen chloride by addition of a few ml of methanol and distilling it off. The resulting 2-exo-amino-3,4-endo-dihydroxy-8-methoxy-7-oxabicyclo[4,3,0]nonane hydrochloride racemate, consisting of the compound of the formula

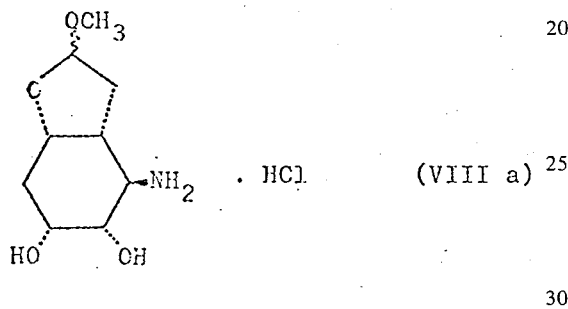

(VIII a)

and its optical antipode, melts at 242°–244°C.

A solution of 35 mg of this hydrochloride in 5 ml of water is charged on to anion exchanger column (Dowex-1OH) and eluted with 250 ml of water. The aqueous solution is concentrated to leave as residue the free racemic 2-exo-amino-3,4-endo-dihydroxy-8-methoxy-7-oxabicyclo[4,3,0]nonane which melts at 96°C.

From the 8S-4β-amino-9,10-dioxatricyclo[4,3,1,0³,⁸]decan-5α-ol there is obtained in analogous manner the 6S-2-exo-amino-3,4-endo-dihydoxy-8-methoxy-7-oxabicyclo[4,3,0]nonane hydrochloride; m.p. 235°–6°[α]$_D$ = –117° (c = 1 chloroform)

EXAMPLE 14

A solution of 45.6 mg of racemic 9,10-dioxatricyclo[4,3,1,0³,⁸]dec-4-ene and 10 mg of p-toluenesulphonic acid in 1.0 ml of methanol is stirred for 45 minutes at room temperature, treated with 3 ml of sodium bicarbonate solution (8%) and extracted 3 times with ethyl acetate. The combined extracts are dried over sodium sulphate and evaporated in vacuo. The oily residue is the racemic 4-endo-hydroxy-8-methoxy-7-oxabicyclo[4,3,0]non-2-ene(thin layer chromatography on silica gel with ethyl acetate as eluant, Rf: 0.36) consisting of the compound of the formula

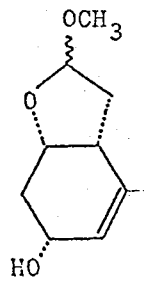

and its optical antipode.

EXAMPLE 15

A solution of 51 mg of the racemic 4-endo-hydroxy-8-methoxy-7-oxabicyclo[4,3,0]non-2-ene in 3 ml of methylene chloride is stirred at room temperature for 26 ½ hours in the presence of 1.1 equivalent of meta-chloroperbenzoic acid and an excess of potassium bicarbonate. Then 5 ml of methylene chloride are added, the mixture is extracted with 3 ml of 2% sodium bicarbonate solution, and the methylene chloride phase is dried over sodium sulphate and evaporated in vacuo. The residue is chromatograhed on 7 g of aluminium oxide (activity level IV), in the course of which the racemic mixture consisting of 2,3-exo-epoxy-4-endo-hydroxy-8-methoxy-7-oxabicyclo[4,3,0]nonane of the formula

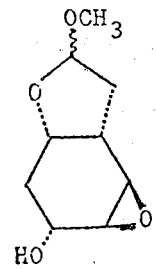

and its optical antipode is eluted with methylene chloride. Elution with ethyl acetate/methanol (9:1) yields the racemic mixture consisting of 2,3-endo-epoxy-4-endo-hydroxy-8-methoxy-7-oxabicyclo[4,3,0]nonane of the formula

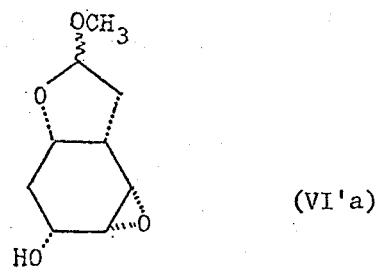

(VI'a)

and its optical antipode

EXAMPLE 15a

A mixture of 51 mg of the racemic 4-endo-hydroxy-8-methoxy-7-oxabicyclo[4,3,0]non-2-ene, 1 ml of methanol, 183 mg of benzonitrile, 217 mg of potassium bicarbonate and 34mg of 90% hydrogen peroxide is stirred at room temperature and treated after 17 and 26 hours respectively with 34 mg of 90% hydrogen peroxide on each occasion. After a further 16 hours 3 ml of water and 10 ml of methylene chloride are added. The organic phase is isolated, extracted 3 times with 10% sodium bicarbonate solution, the aqueous extracts are reextracted 3 times with methylene chloride and the combined organic phases are dried over sodium sulphate and evaporated. The benzamide is removed from the resulting reaction product by crystallisation from methylene chloride/pentane and the residue is chromatographed on 7 g of aluminium oxide (activity level IV). Elution with methylene chloride/ethyl acetate (5:1) yields the racemic mixture consisting of 2,3-exo-epoxy-4-endo-hydroxy-8-methoxy-7-oxabicyclo[4,3,0-]nonane and its opticals antipode. Further elution with ethyl acetate/methanol (9:1) yields the racemic mixture consisting of 2,3-endo-epoxy-4-endo-hydroxy-8-methoxy-7-oxabicyclo[4,3,0]nonane and its optical antipode.

EXAMPLE 15b

A solution of 64 mg of the racemic 4-endo-acetoxy-8-methoxy-7-oxabicyclo[4,3,0]non-2-ene, 207 mg of N-bromacetamide in 15 ml of acetone and 6 ml of water is stirred for 16 hours at room temperature and the acetone is subsequently removed in vacuo. The aqueous solution is extracted with altogether 19 ml of methylene chloride and the methylene chloride extracts are washed with 2 ml of 2% sodium thiosulphate solution, dried over sodium sulphate and evaporated. Preparative thin chromatography of the residue on silica gel (methylene chloride/ethyl acetate 4:1) yields a mixture of isomeric bromohydrins. This mixture is stirred for 1 hour in 2 ml of 2.5% potassium hydroxide in methanol and to the mixture are added 20 ml of water and sodium chloride until saturation is reached. The saturated solution is then extracted 4 times with 15 ml of methylene chloride on ach occasion. The methylene chloride solution is dried over sodium sulphate and then evaporated. The residue is resolved analogous to Example 15a into the racemic 2,3-endo-epoxy-4-endo-hydroxy-8-methoxy-7-oxabicyclo[4,3,0]nonane and the corresponding 2,3-exo-epoxy racemate.

The starting material is obtained in the following manner:

A solution of 170 mg of the racemic 4-endo-hydroxy-8-methoxy-7-oxabycicly[4,3,0]non-2-ene in 1.5 ml of acetic anhydride and 5 ml of pyridine is stirred for 5 hours at room temperature. Volatile components are distilled off in a high vacuum, again at room temperature, and the residue is treated with toluene an distillation performed once more. The oily residue is chromatographed on preparative silica gel plates with ethyl acetate. The racemic 4-endo-acetoxy-8-methoxy-7-oxabicyclo[4,3,0]non-2-ene is obtained as an oily product.

EXAMPLE 15c

A solution of 62mg racemic 4α,5α-epoxy-9,10-dioxa-tricyclo[4,3,1,0³·⁸]decane in 6 ml of dry methanol is treated at 0°C with 6 mg of p-toluenesulphonic acid and stirred at the same temperature for 1 hour. Then 50mg of fine by pulverised potassium bicarbonate are added and the mixture is stirred for 5 minutes, filtered and evaporated. The residue consists of a racemic mixture of 2,3-endo-epoxy-4-endo-hydroxy-8-methoxy-7-oxabicyclo[4,3,0]nonane of the formula VI′a and its optical antipode.

EXAMPLE 16

A solution of 30 mg of the racemic 2,3-endo-epoxy-4-endo-hydroxy-8-methoxy-7-oxabicyclo[4,3,0]nonane in 0.3 ml of dioxane and 2 ml of 24% aqueous ammonia is heated in a sealed test tube for 1 hour to 120°C. The product is evaporated in vacuo, whereupon the racemic mixture consisting of 2-exo-amino-3,4-endo-dihdoxy-8-methoxy-7-oxabicyclo[4,3,0]nonane of the formula VIII, and its optical antipode, is obtained as a colourless oil.

EXAMPLE 17

The racemic 2-exo-amino-3,4-endo-dihydroxy-8-methoxy-7-oxabicyclo[4,3,0]nonane hydrochloride (350 mg; 1.46 mmols) and 250 mg (1.84 mmols) of crystalline sodium acetate are dissolved at 0°–5°C in 6 ml of 50% aqueous acetic acid. While stirring and cooling with an ice-water bath, 1.5 ml of a 3 normal sodium nitrite solution are added to the resulting solution in an argon atmosphere within 40 minutes. After a total of 80 minutes, the reaction mixture is neutralised with a suspension of 6 g of sodium hydrogen carbonate in 12 ml of water and extracted repeatedly with methylene chloride. The combined extracts are dried with sodium sulphate and the solvent is then distilled off in vacuo. The oily residue is the racemic 6-exo-formyl-3-methoxy-2-oxabicyclo[3,3,0] octan-7-endo-ol, consisting of the compound of the formula

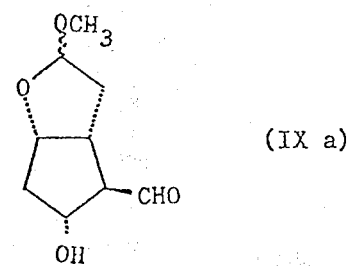

(IX a)

and its optical antipode. Thin layer chromatogram: $R_f = 0.28$ on silica gel with ethyl acetate as eluant.

From the 6S-2-exo-amino-3,4-endo-dihydroxy-8-methoxy-7-oxabicyclo[4,3,0]nonane hydrochloride there is obtained in analogous manner the 1S-6-exo-formyl-3-methoxy-2-oxa-bicyclo[3,3,0]octan-7-endo-ol.

The product is instable and is used at once.

EXAMPLE 17a

A solution of 25 mg (0.123 mmols) of the racemic 2-exo-amino-3,4-endo-dihydroxy-8-methoxy-7-oxabicyclo[4,3,0]nonane in 5 ml of dry ethylene glycol dimethyl ether is treated at 0°C with 120 mg of potassium acetate while stirring, and dinitrogen tetroxide is passed into the solution slowly over the course of 10 minutes Excess dinitrogen tetroxide is then removed by scavenging with nitrogen, the solution is treated with 10 ml of water and 1 ml of saturated sodium carbonate solution and extracted with methylene chloride. The organic extract is dried over sodium sulphate and then evaporated. The residue is the racemic 6-exo-formyl-3-methoxy-2-oxabicyclo [3,3,0]octan-7-endo-ol, which consists of the compound of the formula IXa and its optical antipode.

EXAMPLE 18

A solution of 29.6 mg (0.158 mmols) of freshly manufactured racemic 6-exo-formyl-3-methoxy-2-oxabicylo[3,3,0]octan-7-endo-ol in 3 ml of dry ethylene glycol dimethyl ether is treated with 120 mg (0.32 mmols) of 1-triphenylphosphoranylidene-2-heptanone. (S. M. Miyano et al., Tetr. Letters 1969 1615 and J. Org. Chem. 37. 1810). The resulting solution is refluxed under nitrogen for 11 hours, cooled and concentrated. The residue is purified by preparative thin-layer chromatography on silica gel with ethyl acetate as eluant.

The resulting racemic 3-methoxy-6-exo-(3-oxo-trans-1-octenyl)-2-oxabicyclo [3,3,0]octan-7-endo-ol which consists of the compound of the formula

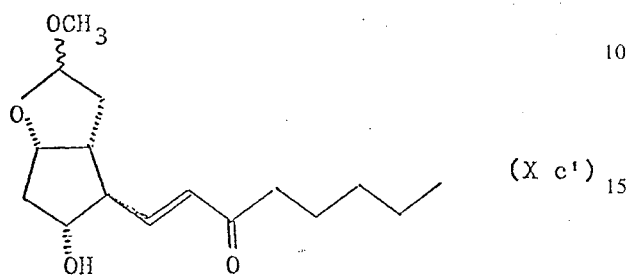

(X c')

and its optical antipode is a yellow oil, which in the infrared zone has absorption maxima at 2.80; 2.90; 5.92; 5.98; 6.15μ and in the ultraviolet zone at 230mμ. The melting point of its 7-endo-(3,5-dinitrobenzoyloxy) derivative (obtained from the above product with 3.5-dinitrobenzoyl chloride and pyridine) is 73°–75,5°C.

EXAMPLE 18a

A solution of 550 mg (2.96 mmols) of the freshly manufactured racemic 6-exo-formyl-3-methoxy-2-oxabicyclo[3,3,0]octan-7-endo-ol in 18 ml of dry ethylene glycol dimethyl ether is treated with 1.39 g (4.4 mmols) of 1-tributylphosphoranylidene-2-heptanone (b.p. 130°C at 0.001 Torr, (S. N. Finch and J. J. Fitt, *Tetr. Letters* 1969 4639). The resulting solution is stirred under nitrogen for 2 hours at 50°C and for 12 hours at room temperature, then concentrated in vacuo. The residue, the racemic 3-methoxy-6-exo-(3-oxo-trans-1-octenyl)-2-oxabicyclo[3,3,0]octan-7-endo-ol is purified by preparative thin layer chromatography on silica gel with ethyl acetate as eluant. (Oil, which congrats to a crystalline solid on standing at −20°, m.p. 8.5°–9.5° C.)

In analogous manner there is obtained from the 1S-6-exo-formyl-3-methoxy-2-oxabicyclo[3,3,0]octan-7-endo-ol the 1S-3-methoxy-6-exo-(3-oxo-trans-1-octenyl)-2-oxabicyclo[3,3,0]octan-7-endo-ol; m.p. 11,5°–13°C [α]$_D^{20}$ = −69± 1°C (c = 1% in chloroform).

EXAMPLE 19

A solution of 50 mg (0.177 mmols) of the racemic 3-methoxy-6-exo-(3-oxo-trans-1-octenyl)-2-oxabicyclo[3,3,0]octan-7-endo-ol in 9 ml of methanol is treated at 0°C while stirring with a solution of 338 mg (8.95 mmols) of sodium borohydride in 3 ml of water. The solution is stirred for 17 minutes at 0°C, then poured on 150 ml of water. The resulting solution is extracted 3 times with 50 ml of chloroform on each occasion, the combined extracts are dried over magnesium sulphate, evaporated, and the residue is dried for 1 hour in vacuo at 25°C and 0.1 Torr. The residual oil is separated into two fractions by preparative thin layer chromatography on silica gel with ethyl acetate as eluant. The less polar fraction consists of the racemic 3-methoxy-6-exo-(3R-hydroxy-trans-1-octenyl)-2-oxabicyclo[3,3,0]octan-7-endo-ol, consisting of the compound of the formula

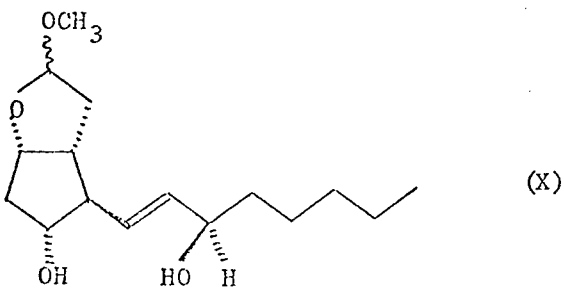

(X)

and its optical antipode (R$_f$ on silica gel with ethyl acetate as eluant 0.31; m.p. of its bis-p-nitrobenzoyloxy derivative, obtained from the above product with p-nitrobenzoyl chloride and pyridine, is 72°–76°C); and the more polar one consists of the racemic 3-methoxy-6-exo-(3S-hydroxy-trans-1-octenyl)-2-oxabicyclo[3,3,-0]octan-7-endo-ol which consists of the compound of the formula

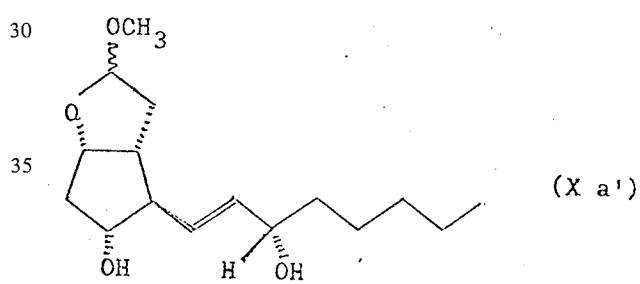

(X a')

and its optical antipode (R$_f$ on silica gel with ethyl acetate as eluant 0,25; m.p. of its bis p-nitrobenzoyloxy derivative is 135°–137.5°).

From the 1S-3-methoxy-6-exo-(3-oxo-trans-1-octenyl)-2-oxabicyclo[3,3,0]octan-7-endo-ol there is obtained in analogous manner the 1S-3-methoxy-6-exo-(3S-hydroxy-trans-1-octenyl)-2-oxabicyclo[3,3,-0]octan-7-endo-ol; oil, [α]$_D^{20}$ = −72±1° (C = 1% in chloroform), and the 1S-3-methoxy-6-exo-(3R-hydroxy-trans-1-octenyl)-2-oxabicyclo[3,3,0]octan-7-endo-ol, m.p. 50°–57° C, [α]$_D^{20}$ = −88±1° (c = 1% in chloroform).

The 3-methoxy-6-exo-(3R-hydroxy-trans-1-octenyl)-2-oxabicyclo[3,3,0]octan-7-endo-ol which occurs as by-product can be led back into the process as follows:

A solution of 50 mg of the racemic 3-methoxy-6-exo-(3R-hydroxy-trans-1-octenyl)-2-oxabicyclo[3,3,0]octan-7-endo-ol in 0.78 ml of methylene chloride is stirred in a nitrogen atmosphere for 17 hours with 782 mg of active precipitated manganese dioxide (Merck, Darmstadt). The mixture is then filtered through diatomaceous earth and evaporated. The residue is the racemic 3-methoxy-6-exo-(3-oxo-trans-1-octenyl)-2-oxabicyclo[3,3,0]octan-7-endo-ol.

I claim:
1. A process for the manufacture of a compound of the formula IX

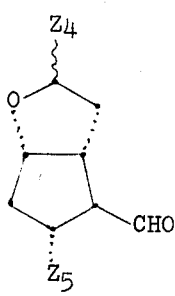 (IX)

in which $Z_4$ and $Z_5$ each independently represents a member of a group consisting of a free hydroxyl group, a hydroxyl group etherified by a lower alkanol, a lower alkanol containing halogen or phenyl, a lower alkanol, in which the methylene group in the α-position is replaced by oxygen, a cycloalkanol with 5 to 7 carbon atoms, a cycloalkanol with 5 to 7 carbon atoms in which the methylene group in the α-position is replaced by oxygen, or by a tri-lower alkylsilyl group, and a hydroxyl group esterified with an aliphatic monocarboxylic acid, an aliphatic dicarboxylic acid, an aromatic monocarboxylic acid or an aromatic dicarboxylic acid, or of the optical antipode and racemate thereof, wherein a compound of the formula VIII

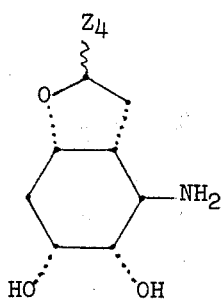 (VIII)

in which $Z_4$ has the meaning given under the formula IX, or the optical antipode or racemate thereof, or an acid addition salt thereof is diazotised with nitrous acid or with a reactive functional derivative thereof.

2. A process according to claim 1, wherein the diazotisation is carried out with nitrous acid.

3. A process according to claim 1, wherein the diazotisaton is carried out in aqueous acetic acid with sodium nitrite.

4. A process according to claim 1, wherein the diazotisation is carried out with an ester or an anhydride of nitrous acid.

5. A process according to claim 1, wherein a compound of the formula IX, in which $Z_4$ represents a hydroxy group etherified with a lower alkanol and $Z_5$ represents a free hydroxy group, or the optical antipode or racemate thereof, is manufactured.

6. A process according to claim 1, wherein a compound of the formula IX, in which $Z_4$ represents the methoxy group and $Z_5$ represents the hydroxy group, or the optical antipode or racemate thereof, is manufactured.

7. A process according to claim 1, wherein a racemic starting material is used.

8. A process according to claim 1, wherein a resulting racemate is resolved into the optical antipodes.

9. A process according to claim 1, wherein an optically active starting material having the 6S-configuration is used.

10. A process according to claim 1, wherein a compound formed at any stage as intermediate product is used as starting material and the remaining step or steps are carried out therewith, or the process is discontinued at any stage.

11. A process according to claim 1, wherein starting materials are formed under the reaction conditions or are used in the form of salts or reactive derivatives.

12. A process according to claim 1, wherein a resulting compound of the formula IX, in which $Z_5$ represents a free hydroxy group, is esterified.

13. A process according to claim 1, wherein a resulting compound of the formula IX, in which $Z_5$ represents a free hydroxyl group, is etherified.

14. A compound of the formula IX

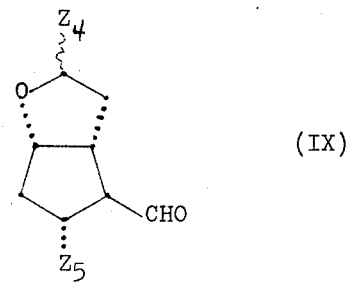 (IX)

wherein $Z_4$ and $Z_5$ each independently represents a member of a group consisting of a free hydroxyl group etherified by a lower alkanol, a lower alkanol containing halogen or phenyl, a lower alkanol, in which the methylene group in the α-position is replaced by oxygen, a cycloalkanol with 5 to 7 carbon atoms, a cycloalkanol with 5 to 7 carbon atoms in which the methylene group in the α-position is replaced by oxygen, or by a tri-lower alkyl-silyl group, and a hydroxyl group esterified with a lower alkanecarboxylic acid, a halosubstituted lower alkanecarboxylic acid, oxalic acid, malanic acid, benzoic acid, benzoic acid substituted by methyl phenyl, nitro or halogen or benzene dicarboxylic acid, and the optical antipode and racemate thereof.

15. A compound of the formula IX according to claim 14, wherein $Z_4$ represents a hydroxy group etherified by a lower alkanol and $Z_5$ represents a free hydroxy group, and the optical antipodes and racemates thereof.

16. The racemate of a compound of the formula IX according to claim 14, wherein $Z_4$ represents the methoxy group and $Z_5$ represents the hydroxy group.

17. A compound of the formula IX according to claim 14, wherein $Z_4$ represents the methoxy group and $Z_5$ represents the hydroxy group, and which has the 1S-configuration.

* * * * *